US007838262B2

(12) United States Patent  
Mian et al.

(10) Patent No.: US 7,838,262 B2  
(45) Date of Patent: Nov. 23, 2010

(54) DETERMINING COPING CAPACITY AFTER EXPOSURE TO A PSYCHOLOGICAL STRESSOR (75) Inventors: Rubina Mian, Coventry (GB); David Whyte MacDonald, Oxford (GB)

(73) Assignee: Oxford Medistress Limited, Birmingham (GB)

( * ) Notice: Subject to any disclaimer, the term of this patent is extended or adjusted under 35 U.S.C. 154(b) by 0 days.

(21) Appl. No.: 10/533,935

(22) PCT Filed: Nov. 5, 2003

(86) PCT No.: PCT/GB03/04749

§ 371 (c)(1),  
(2), (4) Date: May 4, 2005

(87) PCT Pub. No.: WO2004/042395

PCT Pub. Date: May 21, 2004

(65) Prior Publication Data  
US 2006/0014235 A1 Jan. 19, 2006

(30) Foreign Application Priority Data  
Nov. 6, 2002 (GB) ................................ 0225885.3

(51) Int. Cl.  
*C12Q 1/26* (2006.01)

(52) U.S. Cl. ..................................................... 435/25

(58) Field of Classification Search .................... 435/25  
See application file for complete search history.

(56) References Cited

U.S. PATENT DOCUMENTS

| | | | | |
|---|---|---|---|---|
| 5,492,816 | A * | 2/1996 | Pfefferkorn .................. | 435/28 |
| 6,319,953 | B1 * | 11/2001 | Carlson et al. ............... | 514/649 |
| 2005/0112572 | A1 * | 5/2005 | Pincemail et al. ............. | 435/6 |
| 2006/0008544 | A1 * | 1/2006 | Myhill et al. ................ | 424/756 |

FOREIGN PATENT DOCUMENTS

EP 1 262 167 6/2001

OTHER PUBLICATIONS

Kang et al, "Academic Examinations Significantly Impact Responses, but Not lung Function, in Healthy and Well-Managed Asthmatic Adolescents," (Brain, Behavior and Immunity), 1996, vol. 10, pp. 164-181.*
Morrow-Tesch et al, "Heat and Social Stess Effects on Pig Immune Measures," (J. Anim. Sci.), 1994, vol. 72, pp. 2599-2609.*
Tsukamoto, K, "Effects of crowding on immune functions in mice," (Nippon Eiseigaku Zasshi: Jpn J. Hyg.), 1994, vol. 49, No. 4, pp. 827-836.*
Tsukamoto, Kasumasa et al, "Effects of crowding on immune functions in mice," (Japanese Journal of Hygiene), 1994, Vo. 49, pp. 827-836 (English translation of Japanese article).*

Mikawa et, "Perioperative changes in superoxide production in neonates and infants," (Can J Anaesth), 1993, vol. 40, No. 12, pp. 1162-1170.*
Mikawa K. et al. Perioperative Changes in Superoxide Production in Neonates and Infants Canadian J Anaesthesia 40(12)1162-1170, 1993.*
Suzuki K. et al. Capacity of Circulating Neutrophils to Produce Reactive Oxygen Species After Exhaustive Exercise J of Applied Physiology 81(3)1213-1222, Sep. 1996.*
Myhre O. et al. Evaluation of the Probes 2',7'-Dichlorofluoroescin Diacetate, Luminol, and Lucigenin as Indicators of Reactive Species Formation. Biochemical Pharmacology 65(10)1575-1582, May 15, 2003.*
Shult P. et al. Comparison of Superoxide Generation and Luminol Dependent Chemiluminescence with Eosinophils and Neutrophils from Normal Individuals. J Laboratory Clinical Medicine 106(6)638-645, 1985.*
Defauw, Jean M. et al., *Synthesis and Protein Kinase C Inhibitory Activities of Acyclic Balanol Analogs That Are Highly Selective for Protein Kinase C over Protein Kinase A*, Journal of Medical Chemistry, vol. 39, No. 26, 1996, pp. 5215-5227.
Azuma, Yasutaka et al., *Endomorphins delay constitutive apoptosis and alter the innate host defense functions of neutrophils*, Immunology Letters, vol. 81, No. 1, Apr. 1, 2002, pp. 31-40.
Kang, Duck-Hee et al., *The Effect of Psychological Stress on Neutrophil Superoxide Release*, Research in Nursing & Health, Oct. 1994, vol. 17, No. 5, pp. 363-370.
Ferrández, M. D. et al.; *Effects of a Long-Term Training Program of Increasing Intensity on the Immune Function of Indoor Olympic Cyclists*, International Journal of Sports Medicine, Germany, Nov. 1996, vol. 17, No. 8, pp. 592-596.
International Search Report for PCT/GB03/04749 dated Mar. 12, 2004.
Ellard et al, Inter. J. Psychophys. (2001) 41, 93-100.
Hu et al, Cell Signal (1999) 11, 355-360.
Kihara et al, Annals of New York Academy of Sciences (1992) 650, 307-310.
Cohen et al, J. Health & Social Behaviour (1983) 24, 385-396.
Beerda et al, Horm. Behay. (1996) 30, 272-279.
Millspaugh et al, Can. Field-Nat (2000) 114, 196-200.
Rushen in The Biology of Animal Stress Basic Principles and Implications for Animal Welfare (2000) ed. Moberg & Mench, Wallingford:CABI Publishing.
Ellard et al. "The effect of a short-term mental stressor on neutrophil activation" Int'l J. Psychophysiol. 41:93-100 (2001).
Henricks et al. "Stress diminishes infiltration and oxygen metabolism of phagocytic cells in calves" Inflammation 11:427-437 (1987).
Honess et al. "Assessment of stress in non-human primates: Application of the neutrophil activation test" Animal Welfare 14:291-295 (2005).
Kato et al. "Measurement of chemiluminescence in freshly drawn human blood" Klin. Wochenschr. 59:203-211 (1981).

(Continued)

*Primary Examiner*—Ralph Gitomer  
(74) *Attorney, Agent, or Firm*—Nixon & Vanderhye P.C.

(57) ABSTRACT

The present invention provides an in vitro method for quantifying exposure to psychological stress which relies on measuring the retained ability of neutrophils, preferably neutrophils in a whole blood sample, to exhibit challenge-induced superoxide anion production. Using such methodology, coping capacity of individuals for particular psychological stressors may be assessed.

23 Claims, 5 Drawing Sheets

OTHER PUBLICATIONS

McLaren et al. "Leukocyte coping capacity: A novel technique for measuring the stress response in vertebrates" Exp. Physiol. 88:541-546 (2003).

Mian et al. "Of stress, mice and men: A radical approach to old problems" in *Stress and Health: New Research* (K. Oxington ed.) New York: Nova. Sicence Publ., pp. 61-79 (2005).

Thompson et al. "The effect of stress on the immune response of Atlantic salmon (Salmo salar L.) fed diets containing different amounts of vitamin C" Aquaculture 114:1-18 (1993).

Moorhouse et al. "Physiological consequences of captive conditions in water voles (*Arvicola terrestris*)" J. Zool. 271:19-26 (2007).

* cited by examiner

DETERMINING COPING CAPACITY AFTER EXPOSURE TO A PSYCHOLOGICAL STRESSOR

This application is the U.S. national phase of international application PCT/GB2003/004749 filed 5 Nov. 2003 which designated the U.S. and claims benefit of GB 0225885.3, filed 6 Nov. 2002, the entire contents of each of which are hereby incorporated by reference.

The present invention relates to in vitro methods of quantifying exposure to psychological stress in an individual, which may be a human or non-human animal. More particularly, the present invention provides a method of quantifying exposure to psychological stress which relies on measuring the retained ability of neutrophils, preferably neutrophils in a whole blood sample, to exhibit challenge-induced superoxide anion production, i.e. produce a "respiratory burst" in response to in vitro activation. Such methodology may also be applied to screen for stress-relieving drugs.

BACKGROUND TO THE INVENTION

Objective, quantitative and practicable measures of psychological stress are pivotal to studies in many branches of vertebrate biology, including wildlife conservation and management, and are also relevant to the farming industry, animal welfare and veterinary services. Techniques for quantifying levels of human stress are important from a medical perspective, but are also of interest for occupational safety and health. An estimated 1 in 10 people in the UK suffer from work related stress (Health & Safety Executive Information sheet: 1/01/EMSU updated February 2002) at a cost of £3.7 billion to society. Stress-related conditions or effects include immune disorders, cardiovascular disease, muscoskeletal and psychological disorders, workplace injury and ulcers.

Various methods have previously been applied in an attempt to assess stress responses, including the perceived stress questionnaire (Cohen et al., J. Health & Social Behaviour (1983) 24, 385-396), measurement of cortisol and hormonal levels in blood, urine, saliva and faeces (Beerda et al., Horm. Behav. (1996) 30, 272-279), haematological values (e.g. Millspaugh et al., Can. Field-Nat. (2000) 114, 196-200) and behavioural observations (reviewed by Rushen in The Biology of Animal Stress Basic Principles And Implications For Animal Welfare (2000) ed. Moberg & Mench, Wallingford:CABI Publishing). However, these approaches have various drawbacks, and may be inappropriate to use in certain situations. The perceived stress questionnaire is subjective, and so cannot provide an objective measure of stress. Furthermore, questions may not always be answered honestly, for example due to cultural reasons, and this measure of stress cannot be used for testing animals or birds. Measurements of cortisol and hormonal levels in, for example, blood and urine, are often used to assess stress in animals, but these measures are not ideal since their levels change throughout the year. There are no absolute terms of reference, and this type of testing is time consuming. Behavioural observations are also often subjective and difficult to quantify.

More recently, it was shown that exposure of human volunteers to a short term mental stressor leads to increased superoxide anion production being observable in neutrophils present in peripheral blood samples (Ellard et al., Inter. J. Psychophys. (2001) 41, 93-100). It has now been found that exposure of both animals and humans to psychological stress can be rapidly and readily quantified by relying on measurement of the retained capacity of neutrophils in peripheral blood samples to produce superoxide anions in response to a challenge by phorbol myristate acetate (PMA), a known chemical-inducer for activating neutrophils (Hu et al., Cell Signal (1999) 11, 355-360). By this means, for the first time, it has proved possible to obtain a quantitative measurement of copying capacity of animals and humans for known or suspected psychological stressors.

SUMMARY OF THE INVENTION

The method of the invention for quantifying stress is based on direct measures of a cellular response which forms part of the armoury of the immune system. It relies on the ability of individuals to mount a challenge-induced immune response after a potentially stressful event. Each individual's capacity to respond to immune challenge is compared with their own baseline level of immune system activity. After exposure to a known or suspected psychological stressor, superoxide anion production in neutrophils is stimulated iii vitro, and the capacity of neutrophils to produce further superoxide is measured, in effect determining the extent to which superoxide production has been diminished by the known or suspected stressful event. The ability of neutrophils to respond to such in vitro challenge after a stressful event is defined as the individual's coping capacity. Individuals with a higher coping capacity have a greater potential superoxide production and, physiologically, are better able to cope with bacterial challenge after stress. Therefore coping capacity is an in vitro assessment of the individual's current physiological status.

In its broadest aspect, the present invention therefore provides a method for determining whether an individual, which may be a mammal, including a human, or a bird, is experiencing changed physiological status arising from a psychological stressor, the method comprising:
(a) contacting a test sample comprising neutrophils obtained from said individual with an inducer capable of stimulating superoxide production in neutrophils under conditions suitable for such stimulation;
(b) determining the increase in superoxide production above basal in said test sample after a time period when neutrophils of the same species in a control sample, which are free or substantially free of stress-induced activation or at least derived from one or more individuals exposed to the same regime minis a factor to be tested as a psychological stressor, will exhibit superoxide production under the same in vitro conditions; and
(c) comparing the increase in superoxide production above basal observed in said test sample with the increase in superoxide production above basal observed in a control sample as defined in (b) above under the same conditions;

wherein lower superoxide production in said test sample is indicative of the effect of a psychological stressor on the individual's physiological status. If need be or desired, the measured superoxide production above basal for each sample may be corrected by reference to the number of leucocytes or neutrophils in the sample (although a range of leucocytes can produce a respiratory burst, neutrophils are responsible for the majority of superoxide production). As indicated above, residual capacity of leucocytes, or more particularly neutrophils, above basal for in vitro-induced superoxide induction can be termed coping capacity.

The control neutrophils may not be entirely free of stress-induced activation but will necessarily be obtained from the same individual or an individual of the same species prior to exposure of the individual to a suspected or known psychological stressor selected for study. For example, Example 1 illustrates application of such methodology to badgers where the additional stress-inducing effect of transport was quantified compared to mere badger capture based on comparing the residual capacity for challenge-induced activation of neutrophils from transported badgers with such residual capacity of neutrophils from captured but not transported badgers (the controls). Example 2 further illustrates application of the invention for quantifying the stress-inducing effect of handling on wild mammals, e.g. wild mammals as may be found in the UK countryside. Indeed, the invention has wide application in the fields of wildlife conservation, veterinary science and animal husbandry for improving animal well-being, as well as applications to humans as further discussed below.

The samples employed in a method of the invention may be most conveniently whole peripheral blood samples and hence such a method provides rapid results and can be utilised in the field or laboratory. Such a method can be used to elucidate psychological stressors or to determine whether an individual is suffering from recent or continued exposure to a psychological stressor. As indicated above, most importantly, for the first time the present invention provides a means of quantifying the ability of individuals to cope with known or suspected psychological stressors.

Hence, in a preferred embodiment, there is provided a method for determining the coping capacity of an individual for exposure to a psychological stressor, wherein prior to step (a) in a method as defined above said individual is exposed to said psychological stressor for a time period whereby neutrophils in an individual of the same species who is susceptible to stress induced by said stressor will exhibit increased superoxide production and wherein the degree of further in vitro induced superoxide production in said test sample above basal determined in step (c) is a measure of coping capacity.

BRIEF DESCRIPTION OF THE DRAWINGS

Example 1 illustrates use of the methodology of the invention to test the prediction that badgers (*Meles meles*) have a lower coping capacity when they are subjected to trapping and then transport than when they are trapped but do not experience the additional stress of transport with reference to the following figures:

Example 2 illustrates use of the invention to quantify stress induced in small wild animals (wood mice and bank voles) by handling with reference to the following figure:

Example 5 illustrates application of the invention to determine if the stress of running a marathon causes a reduction in the ability of the immune system to respond to challenge with reference to the following further figures:

FIG. 5(*a*) shows combined data for 16 marathon runners obtained using blood samples taken pre- and post-marathon and determining the ability of leucocytes in the blood samples to produce superoxide in response to PMA challenge (filled squares: pre-marathon control samples; open squares: post-marathon samples).

FIG. 5(*b*) shows the non-PMA stimulated chemiluminescence measured at the same time points for the same blood samples (filled squares: pre-marathon control samples; open squares: post-marathon samples).

DETAILED DESCRIPTION OF THE INVENTION

A method of the invention may be a carried out on neutrophils obtained from an individual in any manner whereby the neutrophils are in a whole blood sample suitable for chemical-induced superoxide production. For example, in the case of a human, such a sample may be obtained by a simple finger prick. If need be, whole blood samples for use in a method of the invention may be treated with an anticoagulant. A whole blood sample may be utilised directly, with or without an anticoagulant.

A sample to be tested, directly or after further processing, may be obtained during or shortly after exposure of the individual of concern to a suspected or known psychological stressor. Where one or more samples is taken after exposure to a known or suspected psychological stressor, the initial such sample will generally be obtained as soon as possible. Multiple samples from the same individual may be tested taken at different time points during and/or after exposure to a suspected or known psychological stressor, e.g. within 1 to 5 minutes, 10, 15, 20 or 30 minutes of exposure to the suspected or known psychological stressor. Multiple samples may be tested which have been obtained at different time points after exposure to a psychological stressor in order to determine peaking of the stress response and/or the individual's recovery rate. Alternatively, for simplicity and speed, an individual's coping capacity for a known stress factor may be tested at a single time point after exposure to the stress factor. When testing for stress in animals, the sample may be obtained whilst an animal is under anaesthesia.

A sample to be tested in accordance with the invention may be contacted with any chemical inducer which is capable of stimulating superoxide production in neutrophils. The inducer used in the method may be preferably phorbol myristate acetate (PMA), more particularly, for example, the microbial product phorbol 12-myristate 13-acetate obtainable form Sigma. However, alternative inducers which might be employed are well-known. They include N-Formyl-Met-Leu-Phe (fLMP chemotactic peptide), zymosan, lipopolysaccharide or adrenaline. Suitable lipopolysaccharide is obtainable from the cell wall of a gram negative bacterium, for example *E. coli*. A combination of inducers may be employed, e.g. a combination of PMA and fLMP. A suitable concentration of inducer and period and temperature of induction may be determined if need be by simple experimentation. In the case of PMA, typically it may be added to a whole blood sample at about $10^{-6}$ M to $10^{-3}$ M and the temperature of the sample maintained at about 37° C. Superoxide production may be measured at various time points or a suitable single measurement time point may be determined.

The production of superoxide in response to the inducer may be measured by any known means. Preferably, however, chemiluminescent measurement will be employed for convenience coupled with high sensitivity. For this purpose, a suitable amplifier such as luminol (5-amino-2,3-dihydrophthalzine) or isoluminol (6-amino-2,3-dihydro-1,4-phthalazinedione) may be utilised to detect superoxide as described by Hu et al., Cell Signal (1999) 11, 355-360. Chemiluminesence may be conveniently measured using a portable chemiluminometer. In this way, coping capacity for stress factors may be readily quantified even outside of a laboratory. As indicated above, the level of superoxide production may be measured at one time point after the addition of inducer to the sample, or at multiple time points. Typically, superoxide production is measured at multiple time points at intervals of between 1 and 10 minutes, for example every 5 minutes, after addition of inducer, over a total time period of between 5 minutes and 1 hour, for example over 30 minutes. Preferably, the level of superoxide production is measured after a time period when control neutrophils of the same species, which are free or substantially free of stress-induced activation, will exhibit maximal superoxide production under the same in vitro conditions. This time point can be determined by testing samples obtained from individuals who have not been exposed to a psychological stressor, and measuring superoxide production at various time points after addition of inducer. At the preferred time point, it would be expected that the difference between superoxide production in a sample from an individual exposed to stress, and one who has not been exposed to stress, would be at its greatest. Therefore the test is ideally more sensitive to any changes as a result of stress.

The production of superoxide in response to the inducer is compared to the basal superoxide production in the absence of inducer of the same sample, or a further sample taken from the same individual. As indicated above, measured superoxide production in samples may also be divided by the white cell count or neutrophil count to allow for differences in circulating leucocytes in the donors.

A method of the invention may be used to assess individual responses to the same psychological stressor and compare coping capacities between individuals for a particular psychological stressor. For example, two or more individuals, e.g. two or more humans, may be exposed to a known stressor, and their coping capacity measured at the same time point in accordance with the preferred embodiment of the invention set out above. The results can then be compared to find which of the tested individuals has coped the best with exposure to the psychological stressor. An individual with a lower coping capacity as determined by in vitro induced superoxide stimulation in neutrophils is less able to cope with the stressor than an individual with a higher coping capacity determined in the same manner after exposure to the same stressor. This method would therefore be of particular use in situations where, after a stressful event, a rapid assessment of the individual's ability to cope is required or where it is desired to select individuals on basis of better ability to cope than others with a recognised psychological stressor. Such a method could, for example, form part of a job selection procedure for human individuals where the job is known to entail exposure to psychological stress factors.

A method of the invention may also be used to compare the effects of different stressors on the same individual or group of individuals, for example a sample of individuals from the same species. In this case, the individual's coping capacity in response to each stressor is quantified and compared, in order to determine which is the most stressful. Alternatively, a putative stressor may be tested to determine if it results in a change in the individual's physiological status which is indicative of stress.

As indicated above, methods of the invention are applicable not only to humans but also non-human mammals and additionally birds. For example, a method of the invention can be applied to farmed animals, such as cattle, pigs, sheep, lambs and poultry, e.g. chickens. Importantly, such a method may be used to assess if farmed animals are suffering from significant stress before slaughter with a view to providing meat products which might be labelled "stress-free". A method of the invention may also be applied to farmed animals with a view to providing a wide range of other products which might be labelled "stress-free" or "obtained from stress-free animals", for example, dairy products such as milk, dried milk, cheese, evaporated milk, condensed milks and ice-cream, wool from sheep and lambs tested in accordance with the invention, fine animal hair from animals such as alpacas, llamas, camels, yaks and goats tested in accordance with the invention and coarse animal hair for brushmaking. A method of the invention may be applied to chickens for the purpose of obtaining eggs which might be marketed as coming from "stress-free chickens". Methods of the invention may also be applied to farmed animals to improve animal husbandry techniques. For example, such methodology might be applied for certification of farms as "stress-free farms". Methods of the invention also find application in wildlife conservation and care as illustrated by the badger study already mentioned above and further described in Example 1 below.

Methods of the invention may be applied in assessing and improving the ergonomic efficiency of a human working environment. Thus, methods of the invention may have application in office design, furniture design, lighting, colouring and heating of a working environment and design of office equipment such as computers. Methods of the invention may additionally find application in such diverse fields as transport design, design of leisure facilities, e.g. spas and gyms, and shopping facilities to enhance well-being and reduction of stress-factors. They may also find application for certification of animal boarding houses, e.g. for cats and/or dogs, as "stress-free".

It is also envisaged that assessment of coping capacity in accordance with the invention will have many applications in the field of sports science. Example 5 describes using the methodology of the invention to confirm the expectation that the stress of marathon running reduces the ability of the immune system to respond to challenge as evidenced by decreased leucocyte coping capacity in blood samples taken from marathon runners post-marathon. Similar studies applied to sportsmen and sportswomen taking part in other sporting activities may be of value in improving their performance and well-being.

The invention may also be applied in the field of medicine to assess stress of patients ahead of medical treatment, e.g. surgery, to assess stress associated with medical procedures and in optimising such procedures to minimise stress to patients which may aid recovery and reduce risk of further infection.

In a further aspect, the invention also provides a method of screening for a stress-relieving drug, which comprises administering a test compound to an individual, exposing the individual to a psychological stressor, and measuring their coping capacity using a method according to the invention, and comparing their coping capacity after administration of the test compound to their coping capacity in the absence of the test compound, wherein an increase in coping capacity after administration of the test compound is indicative of stress-relieving ability of said test compound.

The individual used in the above screening method may be a human or animal, for example a mouse, rat, hamster, guinea pig or other mammal. The individual is subjected to a stressor, which may be for example an unpleasant stimulus or stressful situation. In humans, the stressor may be completion of a task under time pressure, for example Raven's progressive matrices, or observing a stressful event which may be fictitious or real. In animals, the stressor may be exposure to an unfamiliar environment. For example, a rat may be placed in an unfamiliar environment such as the "elevated cross". The stressor may also be social stress, for example stress may be induced in mice by housing them in individual cages and then introducing a stranger. Other suitable psychological stressors may be identified using a method of the invention for determining exposure to such a stressor.

Suitable test substances which can be tested in the above screening method include combinatorial libraries, defined chemical entities and compounds, peptide and peptide mimetics, oligonucleotides and natural product libraries, such as phage display libraries and antibody products. Typically, organic molecules will be screened, preferably small organic molecules which have a molecular weight of from 50 to 2500 daltons. Candidate products can be biomolecules including, saccharides, fatty acids, steroids, purines, pyrimidines, derivatives, structural analogs or combinations thereof. Candidate agents are obtained from a wide variety of sources including libraries of synthetic or natural compounds. Known pharmacological agents may be subjected to directed or random chemical modifications, such as acylation, alkylation, estelification, or amidification to produce structural analogs.

A stress-relieving drug identified by a screening method as above may be synthesized and/or formulated into a pharmaceutical composition. Formulation with pharmaceutically acceptable carriers and/or excipients may be carried out using routine methods in the pharmaceutical art. Thus the manner of formulation will depend upon factors such as the nature of the substance and the condition to be treated. Any such substance may be administered in a variety of dosage forms. It may be administered, for example, orally (e.g. as tablets, troches, lozenges, aqueous or oily suspensions, dispersible powders or granules), parenterally, subcutaneously, intravenously, intramuscularly, intrasternally, transdermally or by infusion techniques.

Once an individual has been diagnosed as suffering stress by a method of the invention, they may be provided with stress-relieving treatment, for example, they may be administered a known stress-relieving drug. Thus in a still further aspect, the present invention provides use of a stress-relieving drug in the manufacture of a medicament for treating an individual, e.g. a human, who has been identified as suffering stress by a method of the invention. There is additionally provided a method of treating an individual for stress, e.g. by administration of a stress-relieving drug wherein said individual has been identified as suffering from stress by a method of the invention.

A stress-relieving drug for use in such a method may be one that reduces stress, improves or ameliorates the symptoms of stress, or a drug that treats a stress-related disorder. For example, the drug may be a known anxiolytic or antidepressant or an adjunct to such drug therapy, e.g. drugs such as tryptophan The main classes of anxiolytic drugs are benzodiazepines, for example diazepam and alprazolam; $5\text{-HT}_{1A}$-receptor agonists, such as bupirone; and β-adrenoceptor antagonists, for example propranolol. The main classes of antidepressant drug are tricyclic antidepressants, for example imipramine and amitriptyline; selective serotonin re-uptake inhibitors, for example fluoxetine, fluvoxamine, paroxetine and sertraline; monoamine oxidase inhibitors, such as phenelzine, tranylcypromine, clorgyline and moclobemide; and atypical antidepressants, for example nomifensine, maprotiline, mianserin, bupropion and trazodone.

In a still further aspect, the present invention provides a method of testing the efficacy of a proposed stress-relieving treatment which comprises exposing an individual, e.g. a human, to a psychological stressor in the presence and absence of said treatment and determining their coping capacity as described above. The treatment to be tested may be, for example, handling of a device, gadget or toy designed with the aim of bringing stress relief or exposure to a particular environment, e.g. a smell as in aromatherapy, a pattern of light and/or imagery or sound composed with a view to bringing stress relief. Efficacy of any such treatment will be indicated by an increase in challenge-induced superoxide production indicative of an increase in coping capacity.

In a further aspect of the invention, there is provided a device for carrying out a method of quantifying stress according to the invention comprising a portable chemiluminometer together with other components to enable a single device system for quantifying stress. A device of the invention may desirably comprise a portable chemiluminometer linked to a system for analysing the results to provide a stress measurement for each sample.

The following examples illustrate application of the invention to both wild animals and human volunteers.

EXAMPLES

Example 1

Trapping and Transport of Wild Badgers

As indicated above, this study was carried out to test the prediction that transport of badgers causes substantial additional psychological stress compared to trapping of such animals without transport as reflected in lower coping capacity determined from residual capacity of blood neutrophils for in vitro activation.

Methods (a) Trapping and Transporting Badgers

Badgers were trapped in Wytham Woods, Oxfordshire, U.K (for details of the study site and its badger population see Macdonald & Newman (2002) J. Zool. 256, 121-138) in cage traps baited with peanuts in August and November 2001. Badgers were selected because a measure of stress for this species would be immediately useful in studies of its unusual social system (Macdonald & Newman 2002) and its role in the epidemiology of bovine TB. Also, studies, conservation and control of badgers necessitate their capture and handling, so a means of evaluating alternative procedures would be helpful. The particular population was selected because their individual life histories have been monitored for 14 years during which the utilised trapping and handling procedures were refined to the highest welfare standards. Badger traps were set adjacent to badger setts between 14.00 and 17.00 h. Traps were checked each morning between 06.30 and 07.00 h and trapped badgers were transferred to individual holding cages.

Animals were then assigned to one of two experimental regimes: sampling at the site of capture, without transport (non-transported, n=8), or sampling immediately after transport (transported, n=8). Transport consisted of a short ride of less than 10 minutes on a trailer pulled by an all-terrain quad bike. While in holding cages, badgers were covered with a cloth. Badgers were anaesthetised, either at their site of capture or after transport using an intra-muscular injection of ketamine hydrochloride ("Ketaset," Fort Dodge, U.S.A.) at a dose of 0.2 ml/kg. Processing consisted of measurements of body weight and length, and recording the sex and condition of the badger. Other measurements were also taken as part of the ongoing badger population study. Blood was removed by needle venepuncture of the jugular vein, collected into a tube containing the anticoagulant potassium EDTA (BD Vucutainer Systems, Plymouth U.K.) and taken immediately for PMA challenge. Differential cell counts were made from blood smears fixed in alcohol and stained with May-Grunwald and Giemsa stains (minimum of 100 cells per slide).

(b) PMA Challenge and Measurement of Coping Capacity

To measure the background blood chemiluminescence levels, 10 μl of whole blood was transferred into a silicon anti-reflective tube (Lumivial, E G & G Berthold, Germany), to which 90 μl of $10^{-4}$M luminol (5-amino-2,3-dihydrophthalzine; Sigma A8511) diluted in phosphate buffer was added. The tube was then shaken gently. To measure the chemiluminescence produced in response to challenge, a further tube was prepared as above, but with the addition of 10 μl of the microbial product phorbol 12-myristate 13-acetate (PMA;Sigma P8139) at a concentration of $10^{-6}$M. The PMA was dissolved in a small amount of dimethyl sulphoxide (DMSO; Sigma D 5879) and then diluted to a concentration of $10^{-6}$M in PBS. For each tube, chemiluminescence was measured for 30 seconds every five minutes in a portable chemiluminometer (Junior LB 9509 E G & G Berthold, Germany) for a total of 30 minutes. When not in the chemiluminometer, tubes were incubated at 37° C.

Although a range of leucocytes can produce a respiratory burst, neutrophils are responsible for the majority of oxygen free radical production and so leucocyte coping capacity (LCC) was also examined per quantity of $10^9$ neutrophils/l. This also provided a method of examining LCC in relation to the potential effects of changes in the number of circulating neutrophils after stress.

(c) Statistical Analyses

To compare differences in coping capacity in badgers with and without transport, multivariate analysis of variance (MANOVA) was used, with the response at each time interval as dependent variables, and transport regime as a treatment variable. This procedure was carried out on SPSS for Windows release 10.0.5. Data were log transformed prior to the analysis to ensure the data met assumptions of multivariate normality (Tabachnick & Fidell (1996), Using Multivariate Statistics, Third Edition, New York: HarperCollins College Publishers). Wilcoxon Signed Ranks Tests were used to compare an individual's coping capacity with its basal response.

(d) Animal Welfare Considerations

The badger population at Wytham Woods is under long-term scientific investigation, and badgers are trapped and transported regularly throughout their lives. Examining transport stress is part of continuing refinement of best practice. Work was carried out under English Nature licence 1991537 and Home Office licence PPL 30/1826.

Results

Figure 1:
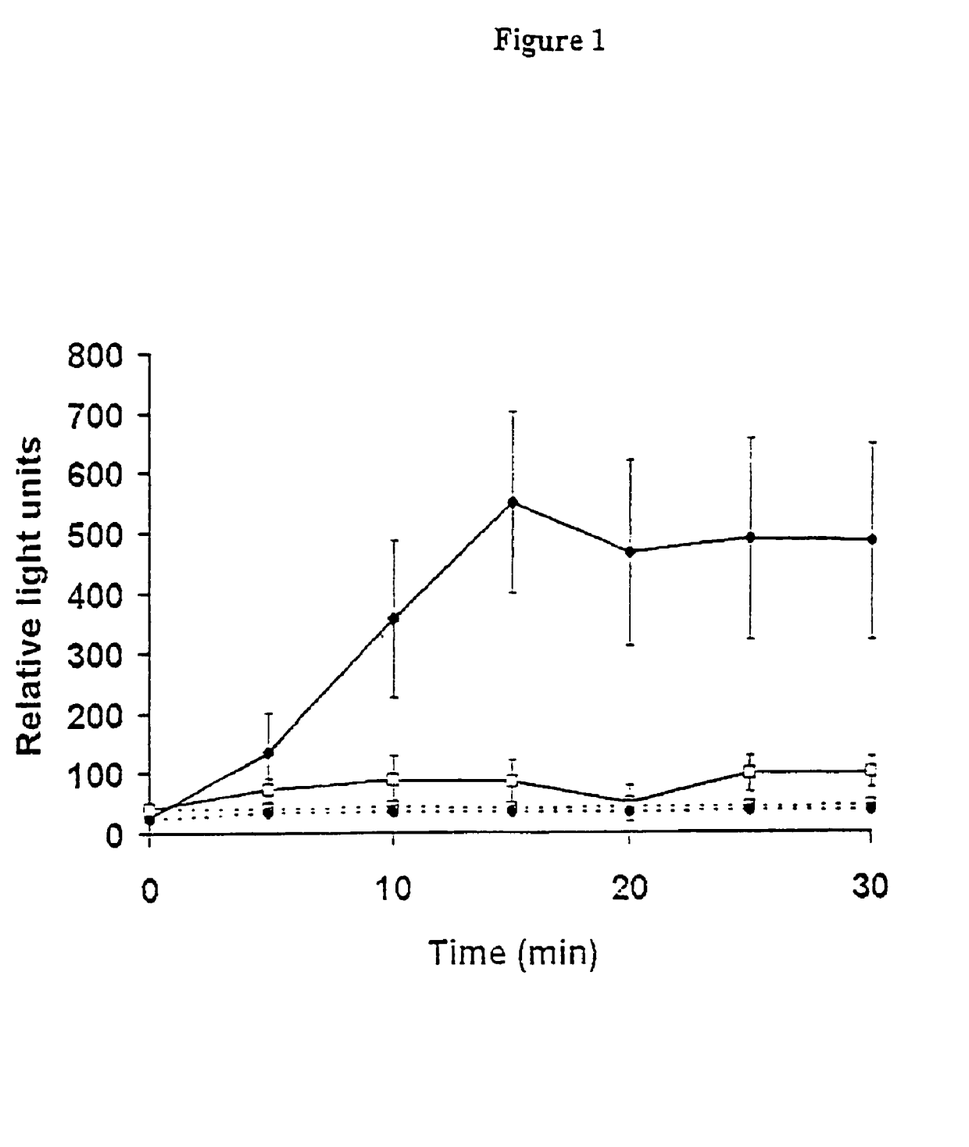
FIG. 1 shows coping capacity measured as relative light units (solid lines, mean±SE) in 8 badgers after transport (square), and 8 badgers without transport (circle) as determined by chemiluminescence measurement of superoxide production in whole blood after challenge with PMA. Dashed lines represent basal leucocyte activity.

Basal superoxide production in and coping capacity in two groups of animals, transported (n=8) and non-transported (n=8), are shown in FIG. 1. Transport significantly reduced coping capacity in badgers ($F_{7,8}$=4.5, p<0.05). The difference in coping capacity between transported and non-transported individuals was greatest at 15 minutes ($F_{1,14}$=8,9, p<0.05; FIG. 1). However, two of the non-transported individuals were caught during a night when ambient temperatures unexpectedly fell below freezing, and these individuals did not show a typical response for this group, and in both cases their coping capacity was no greater than their basal response (Wilcoxon Signed Ranks Test, for both cases Z<−1.0, p>0.1). The transport regime had no effect on basal superoxide production ($F_{7,8}$=2.5, p>0.05). However, to ensure that there was no bias in the LCC results because of individual differences in unstimulated levels of chemiluminescence, we subtracted the basal from the PMA-stimulated values for each animal (PMA-unstimulated).

Transport had an effect on the PMA-unstimulated values from 10 minutes ($F_{1,14}$=4.1; P=0.06) with the difference peaking at 15 minutes ($F_{1,14}$=9.4; P-0.008) and thus showed a pattern consistent with the LCC values described above.

Figure 2:
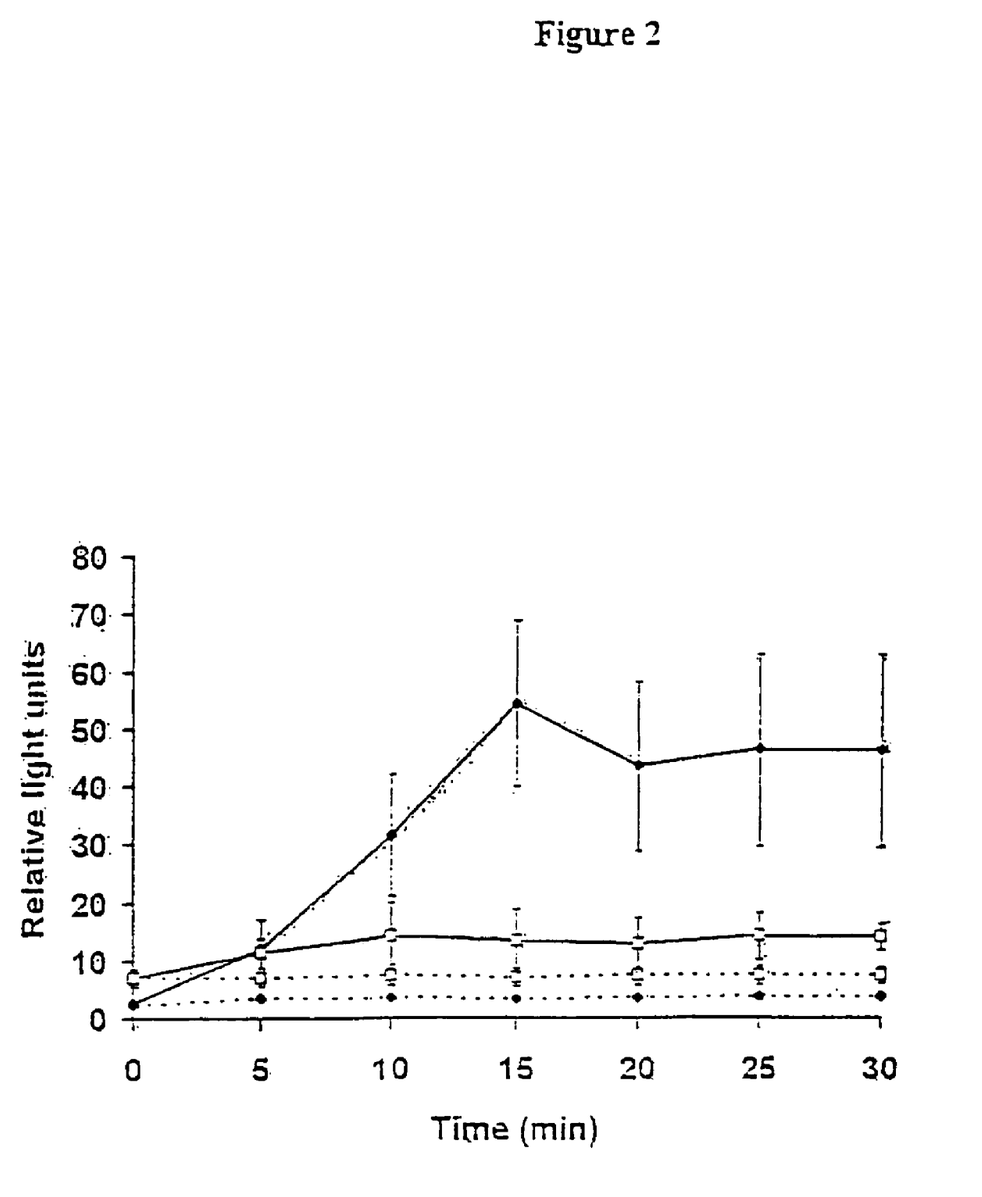
FIG. 2 shows coping capacity calculated as relative light units (RLU) per $10^9$ neutrophils $l^{-1}$ Solid lines represent coping capacity (mean±SE) in badgers after transport (square), and without transport (circle). Dashed lines represent basal activity.

There were differences in the number of leucocytes between the two groups, with transported individuals having significantly lower numbers of leucocytes (Mann-Whitney U=11.0, p<0.05). In addition, leucocyte composition also differed between the groups: transported animals had a higher percentage of neutrophils (Mann-Whitney U=13.5, p=0.05), and a correspondingly lower percentage of lymphocytes (Mann-Whitney U=7.5, p<0.01). Calculation of LCC per $10^9$ neutrophils $l^{-1}$ gave the same pattern as overall LCC, indicating that activity per neutrophil was greater in non-transported individuals (see FIG. 2).

These results indicate that stress dramatically reduces the potential of circulating leucocytes to produce free radicals and support that coping capacity is a quantifiable measure of the stress associated with a specific event. The rather uniform depression of the coping response in all transported individuals suggests that this stressor over-rode the sources of individual variation that characterised the coping responses of non-transported individuals.

Example 2

Quantification of Stress Induced by Handling of Wild Small Animals

The purpose of this study was to investigate the stress response to handling in small wild animals, more particularly in wood mice (*Apodemus sylvaticus*) and bank voles (*Clethrionomys glareolus*), by measuring the ability of animals' circulating leucocytes to produce superoxide in response to PMA challenge.

Methods (a) Experimental Design

One group of animals was handled in the same way as for ecological or behavioural studies and then anaesthetised. Handling brings about a stress response typified by an increased heart rate and attempted escape behaviour and handling is generally stressful for wild animals. Another group of animals was anaesthetised without handling. Handled animals were removed from their traps by gently tipping them into a plastic bag, and were then handled by their scruff, identified to species and placed in a holding pot and anaesthetised. Non-handled animals were anaesthetised in their traps, without being removed and handled. Initially, the front door of the each trap was opened and the animal inside briefly observed to ensure it was in a suitable condition for undergoing anaesthesia. All traps were then left in a dark, quiet room for at least 30 minutes prior to the experiment to ensure the initial observations did not interfere with the experiment. The non-handled animals served to provide a comparative sample of animals that could be used to determine if handling causes supression of coping capacity. All animals were anaesthetised using a mixture of oxygen and isoflourane (Mathews et al., Vet. Rec. (2002) 150, 785-787).

The small mammals used in the study were trapped overnight in Longworth live-traps placed in pairs at 5 m intervals along hedgerows on two commercial dairy farms in South-West England. Traps were baited with approx 14 g of 'Josie' rabbit food (Delta Pet Foods Ltd., Llandovery, Camarthenshire, UK), and apple (approx 5 g) as a source of food and water. Laboratory trials revealed that this bait mix is readily consumed by both species. The amount of bait provided meant that food was effectively available ad libitum during the period in the trap. Traps were set at 1500 hours and collected at 0800 hours the next morning.

While under anaesthesia, the animal's sex and reproductive status (based on testes status in males and indications of mating or pregnancy in females) was determined. Only males and females were included in the study which were in breeding condition. Animals were then weighed to the nearest 0.1 g on a digital balance and their body length from snout to vent measured to the nearest 1 mm. Some juveniles were considered to be too small for sampling, and as a result only adult animals (15 g and over) were included in the analyses. Animals were also given an individual fur clip mark that could be used to later identify them if they were recaptured. As an index of the resources available to the animal, body weight was used. This was appropriate because, for small mammals, body weight is more closely related to the level of stored reserves than calculated body condition indices. We also recorded the presence or absence of fleas, since the presence of these relatively common parasites could potentially influence the animal's energy balance. Work was carried out under Home Office Licence PPL 30/1826.

TABLE 1

Details of the forty animals used in the study.

|  | Wood Mice | Bank voles |
|---|---|---|
| Handled | 9 | 16 |
| Not handled | 6 | 9 |
| Weight range, mean (SD) | 23.0 (3.1) | 22.6 (2.3) |
| Fleas: |  |  |
| present | 7 | 8 |
| absent | 8 | 17 |

(b) PMA Challenge and Measurement of Coping Capacity

Blood was removed from the animals by tail venepuncture and 30 µl was collected from each animal in a heparinised capillary tube. To measure the unstimulated blood chemiluminescence levels, 10 µl of whole blood was transferred into a silicon anti-reflective tube (Lumivial, E G & G Berthold, Germany), to which 90 µl of $10^{-4}$ M luminol (5-amino-2,3-dihydrophthalzine; Sigma A8511) diluted in phosphate buffer was added. The tube was then shaken gently. To measure chemiluminescence produced in response to challenge, a further tube was prepared as above, but with the addition of 10 µl phorbol 12-myristate 13-acetate (PMA; Sigma P8139) at a concentration of $10^{-4}$ M. The PMA was dissolved in a small amount of dimethyl sulphoxide (DMSO; Sigma D 5879) and then diluted to a concentration of $10^{-4}$ M in PBS. For each tube, chemiluminescence was measured every five minutes in a portable chemiluminometer (Junior LB 9509 E G & G Berthold Germany) for a total of 30 minutes. When not in the chemiluminometer, tubes were incubated at 37° C. Leukocyte coping capacity (LCC) was calculated for each individual as the whole blood chemiluminescence measured in response to PMA challenge minus the chemiluminescence measured in unstimulated whole blood.

(c) Statistical Analyses

To compare differences in coping capacity with and without handling, a multivariate GLM (General Linear Model) was used. The chemiluminescence levels at each time interval were the dependent variables. This approach was chosen because it allowed examination of the effect of the treatment at each time interval, giving more detail on the nature of the effects of the treatment and permitted identification of the time interval at which the treatment effect was greatest. Univariate GLM was also used to examine the factors which significantly affected peak coping capacity. The coping capacity values were log transformed prior to the analyses to meet the GLM requirement of normality of data. A small number of negative values (no smaller than −10) were treated as zeros. This procedure was carried out on SPSS for Windows release 10.0.5.

Results

Figure 3:
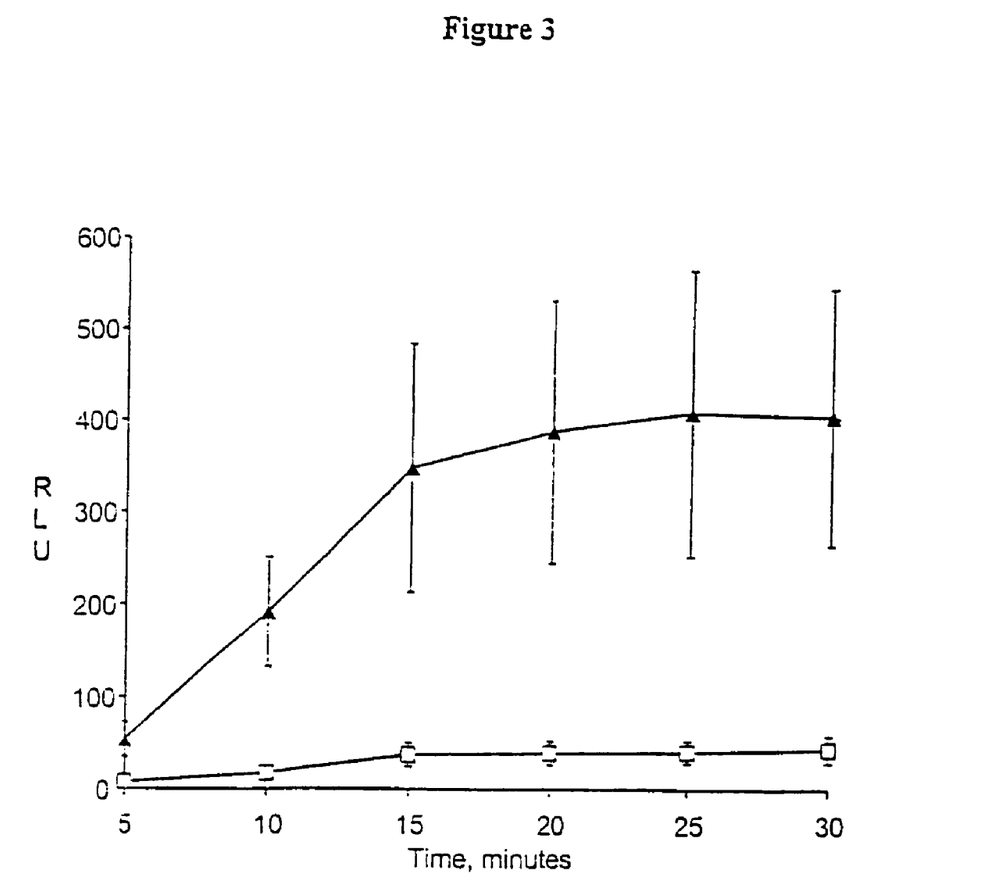
FIG. 3 shows coping capacity measured in relative light units of handled animals (lower line) compared to non-handled animals (upper line) as determined by chemiluminescence measurement of superoxide production in whole blood samples after challenge with PMA.

Forty animals were caught for this study and of these 25 were handled (16 bank voles and 9 wood mice) and 15 were not handled (9 bank voles and 6 wood mice) prior to anaesthesia. Handling brought about a marked reduction in LCC, and reduced the variation in LCC (see FIG. 3). A multivariate GLM revealed that handling significantly reduced LCC ($F_{6,33}$=5.1, P=0.001) and this was the case at all time intervals (5 minutes $F_{1,38}$=9.9, P=0.003; 10 minutes $F_{1,38}$=20.7, P=0.001; 15 minutes $F_{1,38}$=26.3, P=0.001; 20 minutes $F_{1,38}$=30.4, P=0.001; 25 minutes $F_{1,38}$=24.9, P=0.001; 30 minutes $F_{1,38}$=22.7, P=0.001). There was no effect of species in the model, either as a variable on its own ($F_{6,31}$=0.3, P=0.9) or as an interacting variable with handling treatment ($F_{6,31}$=0.4, P=0.9).

LCC was most variable for handled and non-handled animals after 25 minutes, which was also the peak of LCC. Even given the more uniform response of handled animals, the range of LCC in these individuals after 25 minutes was 220 relative light units (minimum −10, maximum 210, mean 39.3, SD 62.9). AGLM was created using the LCC data at 25 minutes ($LCC_{25}$), which included treatment, treatment×body weight interaction and treatment×flea interaction. This model indicated that at $LCC_{25}$ there was a significant treatment× body weight interaction ($F_{2,35}$=4.1, P=0.024), but no evidence of a significant treatment×flea interaction ($F_{2,35}$=0.34, P=0.91). To explore the treatment×body weight interaction further we created individual GLMs for handled and non-handled animals. These models indicated that body weight was significantly and positively associated with $LCC_{25}$ in non-handled animals (FIG. 2; $F_{1,13}$=5.6, P=0.034), but this relationship was lost when animals were handled ($F_{1,23}$=0.6, P=0.42).

This study thus again indicates that leucocyte coping capacity is a quantifiable measure of stress. Handling, a recognised stressor, suppressed the response of circulating leukocytes to PMA. There was no evidence that the level of suppression brought about by handling was related to the animal's body weight, although heavier non-handled animals had a greater peak LCC value. There was variation in the response of handled animals to PMA, albeit much reduced in comparison with the response of animals that had not been handled, but no evidence was found to support that the level of resources available to individual animals could explain this variation.

Example 3

Observing a Fictitious Stressful Event

The purpose of this study was to assess the effect of watching a potentially stressful event on human volunteers.

Methods (a) Subjects

Local ethical committee approval from Coventry University Ethics Committee and informed consent was obtained before this study commenced, in accordance with the declaration of Helsinlki. 14 subjects all moderately fit and healthy aged between 20-26 participated in the study. Exclusion criteria included suffering from psychiatric illness, respiratory or cardiovascular disease, smokers, or prescription medicine taken within the previous month.

(b) Design

The experiments were performed in the afternoon according to highly standardised procedures. Subjects were instructed to avoid exercise or alcohol for 48 hours before the study and be fasting for 2 hours before the study began. Both groups sat quietly for 15 minutes to obtain resting blood pressure, heart rate and resting blood samples. Blood samples were then taken from all subjects 15 minutes before being exposed to either no stress (control conditions) or psychological stress in the in the form of exposure to the horror film. This time point was designated −15 minutes. Subjects had no prior knowledge as to which group they would be assigned to.

8 subjects were exposed to psychological stress in the form of an 83-minuite horror film that none of the subjects had previously seen (The Texas Chainsaw Massacre, 1974, directed and produced by Tobe Hooper, Everett Collection, Inc). The remaining 6 subjects acted as a control group. They were instructed to sit quietly for the same length of time (83 minutes), under similar lighting conditions and were given emotionally non-stimulating material to read if they so wished. This consisted of text books, articles from journals and health information leaflets. A repeated measures design was implemented with two groups: the experimental group (watching the horror film) and a control group. Blood samples, heart rate and blood pressure measurements were taken 15 minutes before, and just after (85 minutes) being exposed to either the 'stressful event' or to control conditions.

(c) Heart Route & Blood Pressure Measurements

A heart rate transceiver (Polar, Heart rate monitor) was attached directly to the chest and heart rate was monitored. Participants were seated, asked to make themselves comfortable, close their eyes and breathe orthonasally. This procedure was carried out for a period of fifteen minutes, in order to minimise possible stress levels experienced prior to, or upon arrival, at the laboratory. At the end of this period baseline heart rate was recorded and the first blood sample taken (see sample protocol below). Participants were then instructed to either read quietly or in a separate room to watch the horror film. Upon completion of the task heart rate was recorded again, and further blood samples taken. Systemic blood pressure (BP) was measured using an aneroid sphygmomanometer (Accoson, (Surgical) Ltd, London) and stethoscope (Harvard Ltd, Edenbridge, UK). Finger stick samples of blood 20 µl were obtained at the specified time points.

(d) PMA Challenge and Measurement of Coping Capacity

To measure the background blood chemiluminescence levels, 20 µl of whole blood was transferred into a silicon anti-reflective tube (Lumivial E G & G Berthold Germany), to which 90 µl of $10^{-4}$M luminol (5-amino-2,3-dihydrophthalzine; Sigma A8511) was added. The tube was then shaken gently. To measure chemiluminescence produced in response to bacterial challenge, 20 µl of phorbol 12-myristate 13-acetate (Sigma P8139) at a concentration of $10^{-3}$M was added. For each tube, chemiluminescence was measured for 30 seconds every five minutes in a portable chemiluminometer (Junior LB 9509 E G & G Berthold Germany) for a total of 30 minutes. When not in the chemiluminometer, tubes were incubated at 37° C. The maximum response to PMA was noted.

(e) Data Analyses

Data are expressed as means±standard deviation from mean. A 2-tailed unpaired t-test was subsequently used to compare the 2 groups at baseline and 85 minutes.

Results

Table 2 shows the differences in the response to PMA between the horror film group (n=8) and the control group (n=6). A highly statistically significant (p<0.05) decrease was found at 85 minutes in the horror film group when compared to the control group. The average heart rate change of +14 for the horror film group represents a 20.6% increase. Their systolic and diastolic blood pressure rose by 10% and 16% respectively. The control group showed no such changes.

TABLE 2

Summary of maximum response to PMA.

| Max response to PMA (RLU) | −15 minutes Baseline | 85 minutes |
| --- | --- | --- |
| Control | 320 (40) | 340 (35) |
| Horror group | 325 (27) | 120 (60)* |

SD in brackets.
*P < 0.05 from control.
RLU = Relative Light Units

Watching a horror movie elicits a psycho physiological arousal which is comparable to Canon's fear flight fight defence reaction, the so called 'stress response' which involves stimulation of the hypothalamus, a change in peripheral resistance and an increase in the release of stress hormones including catecholamines and cortisol. This study also shows that stress affected the responsiveness of a peripheral sample of blood. This can therefore be used as an indictor of stress.

An altered responsiveness to PMA indicates in vivo changes to the state of leukocyte activation. In a state of stress, it is possible that the leukocytes actually release the contents of their granules (and are thus unable to respond to PMA) having already released the contents of their granules. Such leukocytes would be unable to respond to opportunistic infections thus rendering the host more susceptible to disease, as well as potential tissue damage from a host of proteolytic enzymes and oxygen free radicals.

Example 4

Stressor Task

Method (a) Subjects

Local ethical committee approval from Coventry University Ethics Committee and informed consent was obtained before this study commenced, in accordance with the declaration of Helsinki. 12 undergraduate students (aged 18-23 years) were assigned to either an experimental group (given test) or asked to sit quietly for an equivalent time period.

Exclusion criteria included suffering from psychiatric illness, respiratory or cardiovascular disease, smokers, or prescription medicine taken within the previous month.

(b) Stressor Task

The test was a written visual spatial task test comprising 36 questions, on which a 15 minute constraint was imposed (Ravens J. C. Advanced Progressive Matrices, set II, Oxford Psychologists Press, Oxford, 1994). A small finger stick blood sample (Boebringer Mannheim, Soft Clix) was taken before and immediately after task completion. 20 µl of blood was collected in a pipette.

(e) PMA Challenge and Measurement of Coping Capacity

To measure the background blood chemiluminescence levels, 20 µl of whole blood was transferred into a silicon antireflective tube (Lumivial E G & G Berthold Germany), to which 90 µl of $10^{-4}$M luminol (5-amino-2,3-dihydrophthalzine; Sigma A8511) was added. The tube was then shaken gently. To measure chemiluminescence, 20 µl of phorbol 12-myristate 13-acetate (Sigma P8139) at a concentration of $10^{-3}$M was added. For each tube, chemiluminescence was measured for 30 seconds every five minutes in a portable chemiluminometer (Junior LB 9509 E G & G Berthold Germany) for a total of 30 minutes. When not in the chemiluminometer, tubes were incubated at 37° C. The maximum response to PMA was noted.

(d) Data Analyses

Data are expressed as means±standard deviation from mean. A 2-tailed unpaired t-test was subsequently used to compare the 2 groups at baseline and 15 minutes.

Results

Table 3 shows the effect of completing a stressor task on leukocyte responsiveness to PMA. The experimental group had significantly reduced responses to PMA ($p<0.05$, unpaired t test) compared to controls. Therefore completion of a stressor task diminished responsiveness to PMA.

TABLE 3

Summary of maximum response to PMA.

| Max response to PMA (RLU) | Baseline | 15 minutes |
|---|---|---|
| Control | 420 (40) | 380 (25) |
| Experimental Group | 380 (30) | 160 (70)* |

Mean +/− Standard deviation (SD) in brackets.
*P < 0.05 from control.
RLU = Relative Light Units Example 5

Determination of the Effect of Marathon Running on the Ability of Blood Neutrophils to Respond to PMA Challenge in Vitro Study Design Sixteen marathon runners were included in the study who during the course of the study undertook the London marathon. Blood samples were taken from the runners the day before the race and immediately following the race. For each blood sample, basal chemiluminescence and chemiluminescence with PMA-challenge was determined in similar manner as described in previous examples. Chemiluminesence measurements were made at 5 minute intervals up to 35 minutes.

Results

Figure 4:
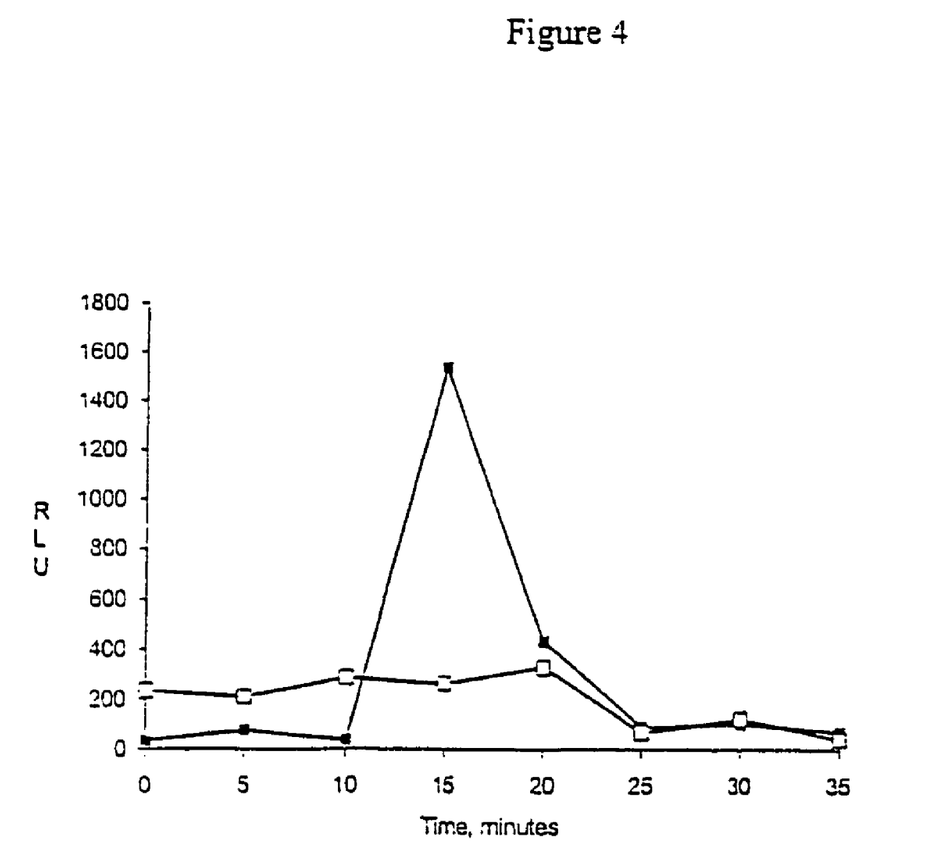
FIG. 4 shows typical data for a single marathon runner obtained using blood samples taken pre- and post-marathon and determining the ability of leucocytes in the blood samples to produce superoxide in response to PMA challenge (filled squares: pre-race control; open squares: response in post-race sample).

FIG. 4 shows typical data for a single runner. On the day before the marathon, the runner showed response to PMA-challenge as demonstrated by the spike in relative light units (RLU) in the pre-race response line. In contrast, the post-race response line shows no such spike.

Figure 5A:
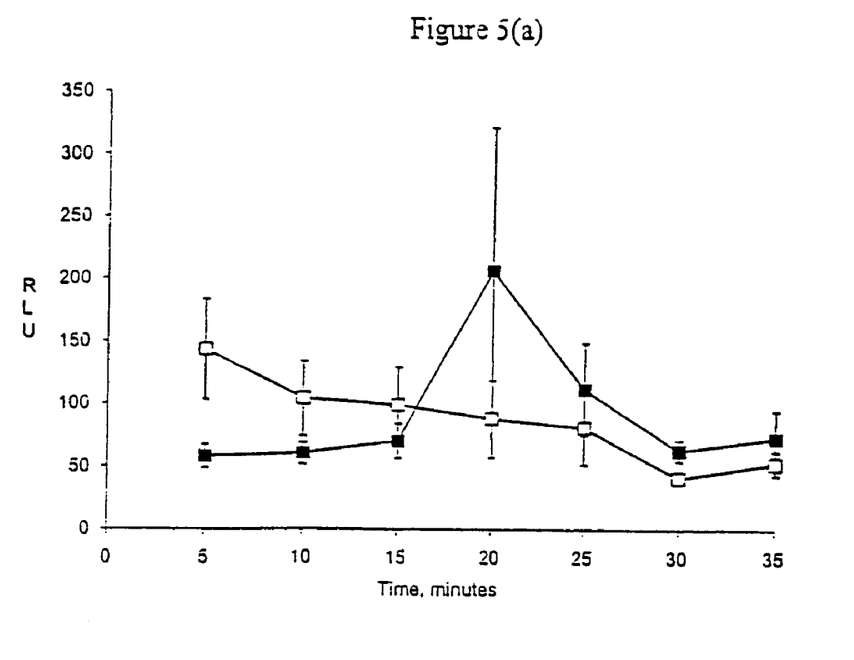
Figure 5B:
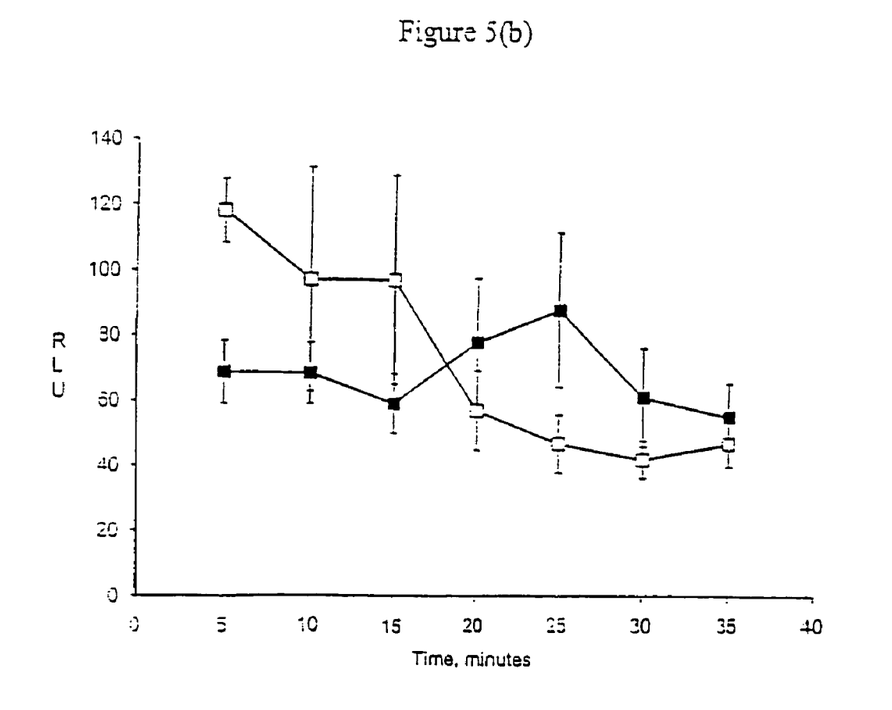

Most pre-race blood samples showed a peak response to PMA-challenge after 15 to 20 minutes (see FIG. 5(a)). The magnitude of the peak response was highly variable. In contrast, the data for post-race samples indicated strong damping of PMA-induced superoxide production compared to the control pre-race samples. The non-PMA stimulated results for the same samples are shown in FIG. 5(b). This data is in keeping with the well-known phenomenon that elite athletes are more at risk from certain types of infection than other people and suggests utility of the invention across a wide range of sporting activities for better understanding of stress in sportsmen and sportswomen and in finding means to ameliorate the effects of stress or reduce stress in such people.

The invention claimed is:

1. A method for determining whether a human or non-human mammal experiences stress effect arising from exposure to a psychological stressor, in which a chemical inducer stimulates superoxide production in a control sample above basal, wherein basal is superoxide production in the absence of said chemical inducer, the method comprising:
   (a) incubating neutrophils in a control sample, which comprises whole blood that is free or substantially free of stress-induced activation or derived from an individual of the same species as said human or non-human mammal and not exposed to said stressor, in the presence of said chemical inducer;
   (b) determining superoxide production in said control sample in the presence of said chemical inducer under in vitro conditions that induce neutrophils to produce superoxide, wherein in said control sample there is increased chemically-induced superoxide production above basal;
   (c) incubating neutrophils in a test sample, which comprises whole blood obtained from said human or non-human mammal taken after exposure to said stressor, in the presence of said chemical inducer;
   (d) determining superoxide production in said test sample in the presence of said chemical inducer under in vitro conditions that induce neutrophils to produce superoxide; and
   (e) comparing increased chemically-induced superoxide production above basal determined in said test sample with increased chemically-induced superoxide production above basal determined in said control sample;
wherein lower increased chemically-induced superoxide production above basal in said test sample compared to increased chemically-induced superoxide production above basal in said control sample is determinative of stress effect caused by said stressor.

2. A method according to claim 1, wherein said test sample is obtained from a human.

3. A method according to claim 1, wherein said test sample is obtained from a farmed animal.

4. A method according to claim 3, wherein the farmed animal is a cow, pig, sheep, lamb or poultry.

5. A method according to claim 1, wherein said test sample is obtained from a wild mammal.

6. A method according to claim 1, wherein the chemical inducer which stimulates superoxide production in neutrophils is phorbol myristate acetate (PMA), N-Formyl-Met-Leu-Phe (fLMP chemotactic peptide), zymosan, lipopolysaccharide or adrenaline.

7. A method according to claim 1, wherein superoxide production is detected using luminol or isoluminol as an amplifier and chemiluminescence is measured.

8. A method according to claim 1, wherein the chemical inducer which stimulates superoxide production in neutrophils is phorbol myristate acetate (PMA), superoxide production is detected using luminol as an amplifier and chemiluminescence is measured.

9. A method of treating a human or non-human mammal suffering from stress which comprises providing a stress-relieving treatment, to a human or non-human mammal identified as suffering from stress using a method according to claim 1.

10. The method according to claim 1, wherein stress effect is experienced, and further comprising measuring coping capacity for exposure to said stressor as residual capacity of neutrophils in said test sample to increase superoxide production above basal after incubation in the presence of said chemical inducer.

11. A method of testing the efficacy of a proposed stress-relieving treatment which comprises exposing a human or non-human mammal to a psychological stressor in the presence and absence of said treatment and determining coping capacity of the human or non-human mammal using a method according to claim 10.

12. A method of screening for a compound having stress-relieving activity, the method comprising:
(a) administering a test compound to a human or non-human mammal;
(b) exposing said human or non-human mammal to a psychological stressor and measuring coping capacity using a method according to claim 1; and
(c) comparing coping capacity after administration of the test compound to coping capacity in the absence of the test compound, wherein an increase in coping capacity after administration of the test compound is indicative of stress-relieving activity of said test compound.

13. A method according to claim 12, wherein the test compound is administered to a non-human mammal.

14. A method according to claim 12, further comprising synthesizing a stress-relieving drug which is a test compound identified by said method, and/or formulating the drug into a pharmaceutical composition.

15. A method for determining whether a human or non-human mammal is experiencing stress effect arising from exposure to a psychological stressor, in which a chemical inducer stimulates superoxide production in a control sample above basal, wherein basal is superoxide production in the absence of said chemical inducer, the method comprising:

(a) contacting neutrophils in a test sample, which comprises whole blood obtained from said human or non-human mammal after exposure to said stressor, with said chemical inducer;
(b) measurimg increased chemically-induced superoxide production above basal in said test sample under in vitro conditions that induce neutrophils to produce superoxide; and
(c) comparing increased superoxide production above basal in said test sample with increased superoxide production above basal in a control sample, which comprises whole blood that is free or substantially free of stress-induced activation or derived from an individual of the same species as said human or non-human mammal and not exposed to said stressor, contacted with said chemical inducer;

wherein lower increased chemically-induced superoxide production above basal in said test sample compared to increased chemically-induced superoxide production above basal in said control sample is determinative of stress effect caused by said said stressor.

16. A method according to claim 15, wherein said test sample is obtained from a human.

17. A method according to claim 15, wherein said test sample is obtained from a farmed animal.

18. A method according to claim 15, wherein said test sample is obtained from a wild mammal.

19. A method according to claim 15, wherein the chemical inducer which stimulates superoxide production in neutrophils is phorbol myristate acetate (PMA), N-Formyl-Met-Leu-Phe (fLMP chemotactic peptide), zymosan, lipopolysaccharide or adrenaline.

20. A method according to claim 15, wherein superoxide production is detected using luminol or isoluminol as an amplifier and chemiluminescence is measured.

21. A method according to claim 15, wherein the chemical inducer which stimulates superoxide production in neutrophils is phorbol myristate acetate (PMA), superoxide production is detected using luminol as an amplifier and chemiluminescence is measured.

22. The method according to claim 15, wherein stress effect is experienced, and further comprising measuring coping capacity for exposure to said stressor as the lower increased chemically-induced superoxide production above basal in said test sample.

23. A method of testing the efficacy of a proposed stress-relieving treatment which comprises exposing a human or non-human mammal to a psychological stressor in the presence and absence of said treatment and determining coping capacity of the human or non-human mammal using a method according to claim 22.

* * * * *